(12) United States Patent
Dragan et al.

(10) Patent No.: US 7,882,588 B2
(45) Date of Patent: *Feb. 8, 2011

(54) DISPOSABLE DENTAL APPLICATOR

(75) Inventors: William B. Dragan, Easton, CT (US); John J. Discko, Trumbull, CT (US)

(73) Assignee: Centrix, Inc., Shelton, CT (US)

( * ) Notice: Subject to any disclaimer, the term of this patent is extended or adjusted under 35 U.S.C. 154(b) by 296 days.

This patent is subject to a terminal disclaimer.

(21) Appl. No.: 10/640,773

(22) Filed: Aug. 14, 2003

(65) Prior Publication Data
US 2004/0031114 A1    Feb. 19, 2004

Related U.S. Application Data

(63) Continuation of application No. 09/549,362, filed on Apr. 14, 2000, now Pat. No. 6,634,051, which is a continuation-in-part of application No. 09/517,549, filed on Mar. 2, 2000, now Pat. No. 6,186,792, which is a continuation-in-part of application No. 08/934,983, filed on Sep. 22, 1997, now Pat. No. 6,049,934.

(51) Int. Cl.
*A46B 9/04* (2006.01)
*A46B 17/02* (2006.01)

(52) U.S. Cl. ............... 15/106; 15/167.1; 15/105; 15/206; 15/143.1; 15/172; D4/105; D4/138; 433/141

(58) Field of Classification Search ............ 15/106, 15/167.1, 105, 206, 143.1, 172, 160, 211, 15/210.1, 164, 107, 110, 114, 118, 111, 159.1; D4/105, 106, 104, 138; 132/218; 433/146, 433/141, 142, 102, 224

See application file for complete search history.

(56) References Cited

U.S. PATENT DOCUMENTS 890,143 A    6/1908  Kuzzer .................. 15/106

(Continued)

FOREIGN PATENT DOCUMENTS

DE    39 37 030 A1    5/1990

(Continued)

OTHER PUBLICATIONS

U.S. Appl. No. 10/264,921, filed Oct. 4, 2002, Dragan.

*Primary Examiner*—Gary K Graham
(74) *Attorney, Agent, or Firm*—Fattibene and Fattibene; Paul A. Fattibene

(57) ABSTRACT

An applicator principally for use in the dental profession, for the placement of different materials as may be required. The applicator includes an elongated handle having an applicating end portion formed at the opposed ends thereof which may be either of like or unlike construction, i.e. formed as a brush and/or a flocked applicating end portion. The flock may extend from the distal end a predetermined longitudinal distance over an extended portion. Intermediate the opposed applicating end portion, the elongated handle is provided with a circumscribing groove to define a frangible area by which the user, at his or her option, can cleanly sever the applicator handle to form two separate and distinct applicators. The applicator is also provided with a hinging arrangement adjacent the opposed applicating end portions whereby the applicating end portions may be angularly bent relative to the elongated handle at the option of the user.

5 Claims, 3 Drawing Sheets

U.S. PATENT DOCUMENTS

| | | | | |
|---|---|---|---|---|
| 2,229,664 | A | | 1/1941 | Meeske .................. 15/106 |
| 2,386,085 | A | | 10/1945 | Babel .................. 15/167.1 |
| 2,803,029 | A | | 8/1957 | Brady .................. 15/106 |
| 3,720,975 | A | | 3/1973 | Nelson .................. 15/206 |
| 3,818,911 | A | | 6/1974 | Fournier .................. 15/244.2 |
| 4,030,199 | A | | 6/1977 | Russell .................. 15/106 |
| 4,165,755 | A | * | 8/1979 | Cassai .................. 132/218 |
| 4,194,848 | A | * | 3/1980 | Kingsford .................. 401/5 |
| 4,527,575 | A | * | 7/1985 | Vasas .................. 132/218 |
| 4,691,404 | A | | 9/1987 | Tarrson et al. .................. 15/167 R |
| 4,712,266 | A | * | 12/1987 | Yamaki .................. 15/167.1 |
| 4,922,936 | A | * | 5/1990 | Buzzi et al. .................. 132/321 |
| 4,958,402 | A | * | 9/1990 | Weihrauch .................. 15/207.2 |
| 4,997,371 | A | | 3/1991 | Fischer .................. 433/90 |
| 5,001,803 | A | * | 3/1991 | Discko, Jr. .................. 15/167.1 |
| 5,009,593 | A | | 4/1991 | Vogelstein .................. 433/221 |
| D329,142 | S | | 9/1992 | Discko, Jr. et al. .................. D4/104 |
| 5,150,495 | A | | 9/1992 | Discko, Jr. et al. .................. 15/167.1 |
| 5,283,924 | A | | 2/1994 | Kaminski et al. .................. 15/244.1 |
| 5,286,257 | A | | 2/1994 | Fischer .................. 604/82 |
| 5,350,298 | A | | 9/1994 | Delaire .................. 433/81 |
| 5,414,890 | A | | 5/1995 | Morendo .................. 15/167.1 |
| 5,459,898 | A | | 10/1995 | Bacolot .................. 15/106 |
| 5,604,952 | A | | 2/1997 | Zeleznick .................. 15/167.1 |
| 5,623,941 | A | * | 4/1997 | Hedberg et al. .................. 600/569 |
| 5,632,620 | A | | 5/1997 | Musikant et al. .................. 433/102 |
| 5,647,746 | A | | 7/1997 | Chipman .................. 433/226 |
| 5,693,360 | A | * | 12/1997 | Stern et al. .................. 427/2.29 |
| 6,049,934 | A | | 4/2000 | Discko .................. 15/106 |
| 6,059,570 | A | | 5/2000 | Dragan et al. |
| D435,105 | S | | 12/2000 | Dragan et al. |
| 6,186,792 | B1 | | 2/2001 | Discko .................. 433/220 |
| 6,288,138 | B1 | | 9/2001 | Yamamoto et al. |
| 6,328,159 | B1 | | 12/2001 | Discko, Jr. |
| 6,386,872 | B1 | | 5/2002 | Mukasa et al. .................. 433/90 |
| D458,456 | S | | 6/2002 | Dragan et al. |
| D461,247 | S | | 8/2002 | Dragan et al. |
| 6,482,207 | B1 | | 11/2002 | Errico .................. 433/149 |
| 6,634,051 | B1 | * | 10/2003 | Dragan et al. .................. 15/106 |
| D489,535 | S | | 5/2004 | Dragan |

FOREIGN PATENT DOCUMENTS

| | | | |
|---|---|---|---|
| DE | 39 37 030 C2 | 5/1990 | |
| EP | 0656195 | * 6/1995 | |
| EP | 0903115 | * 3/1999 | |
| FR | 1273139 A | 10/1961 | |
| GB | 7787 | 6/1886 | .................. 15/167.1 |
| GB | 561300 | 5/1944 | .................. 15/106 |
| GB | 2 230 180 A | 10/1990 | |

\* cited by examiner

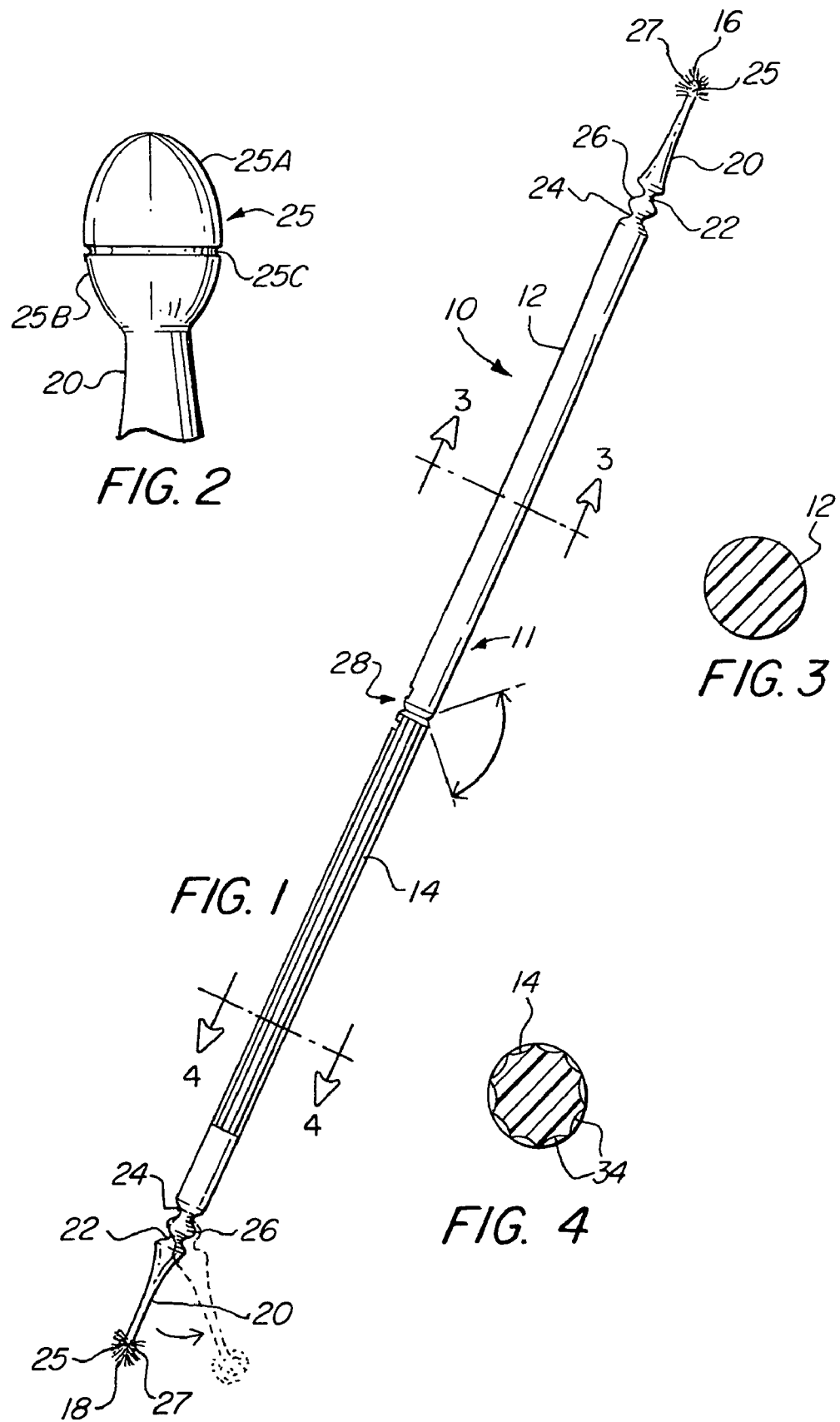

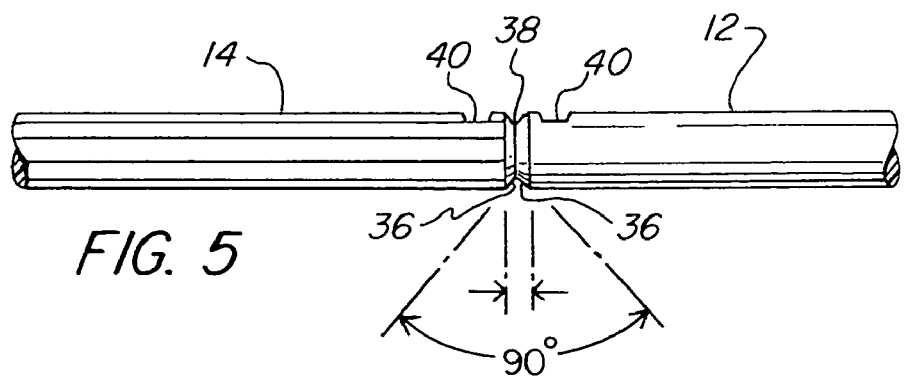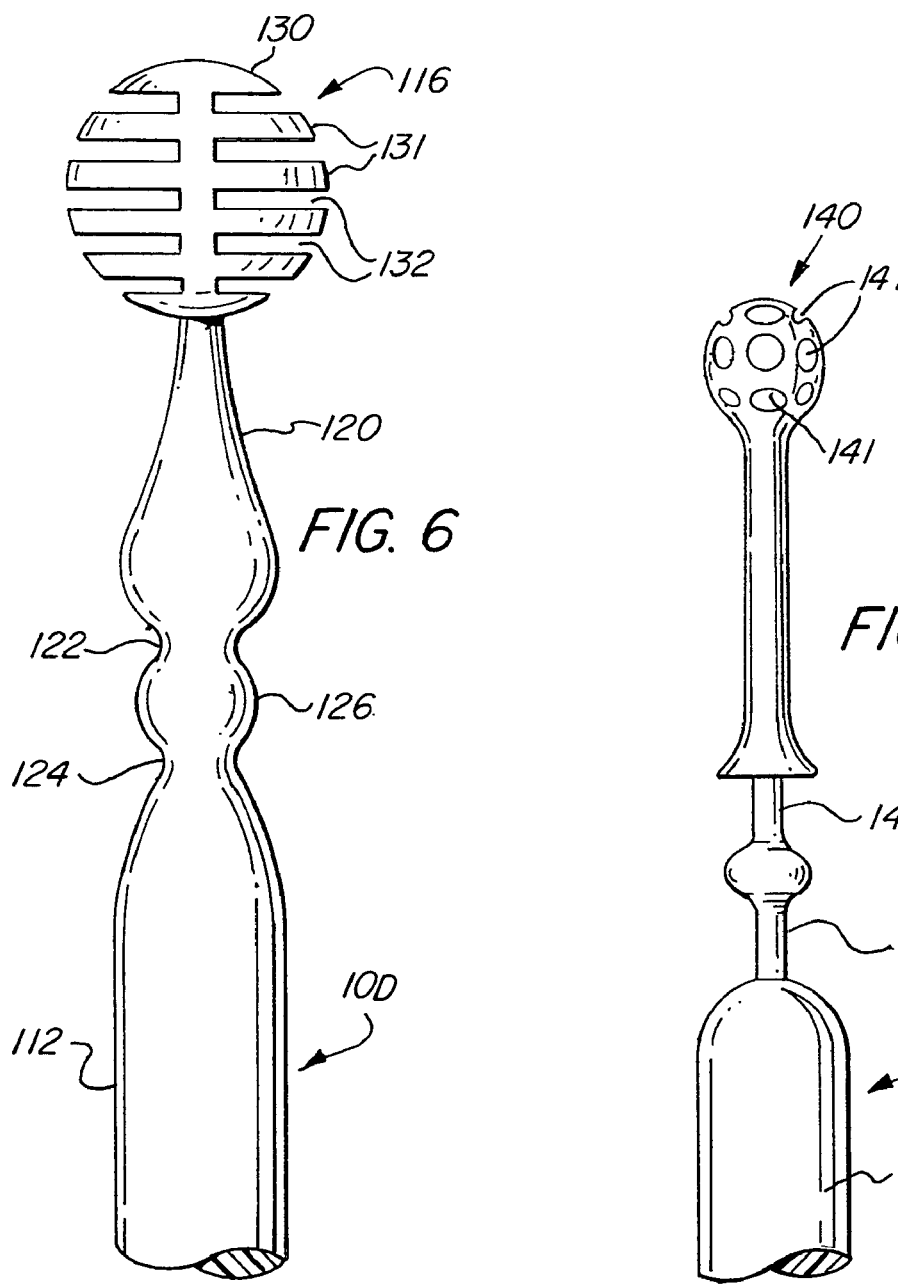

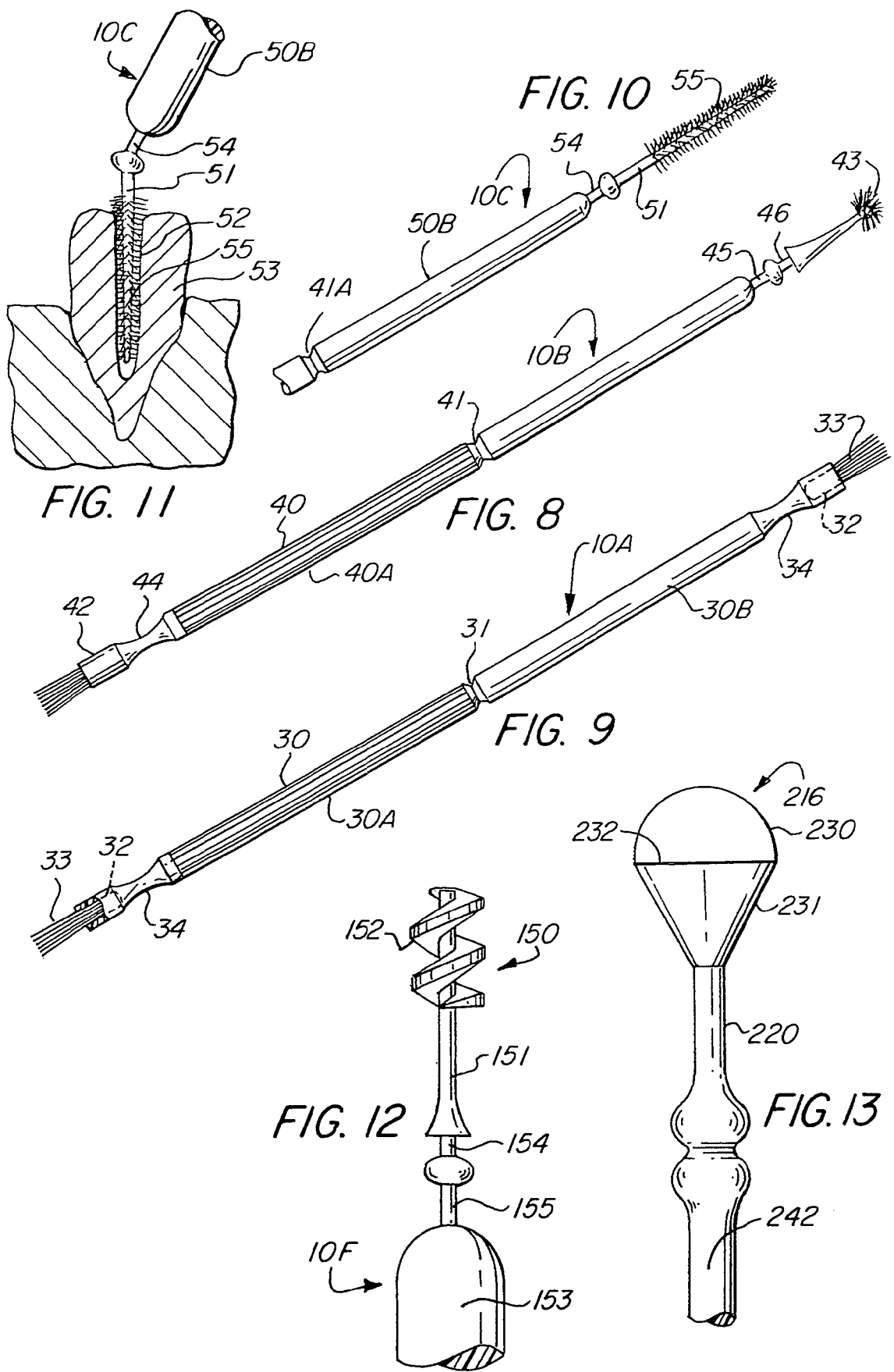

DISPOSABLE DENTAL APPLICATOR

RELATED APPLICATIONS

This application is a continuation application of application Ser. No. 09/549,362, filed Apr. 14, 2000, now U.S. Pat. No. 6,634,051, which is a continuation-in-part application of application Ser. No. 08/934,983 filed Sep. 22, 1997, now U.S. Pat. No. 6,049,934, and a continuation-in-part application of application Ser. No. 09/517,549 filed Mar. 2, 2000, now U.S. Pat. No. 6,186,792, all of which are herein incorporated by reference.

FIELD OF INVENTION

The present invention relates to disposable applicators for applying various materials, and more specifically to a double ended disposable dental applicator having either a double ended brush applicating end, or a double ended flocked applicating end, or having a flocked applicator on one end and a brush applicator on the other end.

BACKGROUND OF THE INVENTION

Applicators such as brushes, foam pads, cotton swabs or other applicators, are used to apply a variety of materials in many applications. Such applicators are of particular use in dentistry for applying various dental materials. Due to the risk of cross-contamination, it is desirable to use an applicator only once, after which the applicator is discarded. As a result, it is necessary to produce an applicator that is efficient and easy to handle and at a low cost. A disposable dental brush is disclosed in U.S. Pat. No. 5,150,495 issuing to Discko et al on Sep. 29, 1992, entitled "Disposable Dental Brush", which is also herein incorporated by reference. Therein disclosed is a disposable dental brush for applying various dental materials that includes an elongated handle having a tuft of bristles constructed so as to allow the portion thereof adjacent to the brush end to be readily bent so as to angularly dispose the brush end relative to the longitudinal axis of the handle. Also disclosed therein is a brush end comprising a relatively short tubular holder or sleeve which has a bore extending therethrough such that the brush end is detachably connected to the free end of a handle by a frictional retention in the tubular brush holder. The dentist may use this construction as a single ended dental brush or alternatively, as a double ended brush, which allows the dentist to use the same brush for working with and applying different materials to a patient's teeth. Upon completion of a given procedure, the brush end or ends are rendered readily disposable. While this brush configuration has been adequate, it is not without some inconveniences. For example, the brush end that attaches to the handle is relatively small and difficult to manipulate and place on the handle. This is especially difficult when a dentist is wearing gloves. Additionally, the short brush portion results in the attached handle sometimes being inserted into the patient's mouth. This compromises the use of the attached handle portion in that it must be disinfected. Therefore, there is a need for an improved disposable applicator that is easy to handle, is inexpensive to manufacture, and produces less waste.

Applicators having a flocked end portion are also known as disclosed in German Patent DE 39 37 030 C2. However, it has been observed that due to the limited amount of surface area located at the end of the applicator handle, the amount of flocking fibers that would normally adhere thereto utilizing the teaching of said German patent was quite limited. As a result, the flocked end of the applicator, being sparsely flocked, was capable of holding only a minimum amount of material.

SUMMARY OF THE INVENTION

An object of this invention is to provide a double ended applicator having a frangible portion disposed intermediately of the applicator to provide for a positive and simple frangible point to effect separate and independent use of the respective applicating end portions, if desired.

Another object is to provide for a simple and inexpensive applicator having a handle with a brush applicating end portion on one end of the handle and a flocked applicating end portion on the other end of the handle with a frangible portion disposed intermediately of the respective ends of the handle.

Another object is to provide an applicator having an end portion formed of various shapes to enhance a more uniform distribution of flocking material to the end portion of a handle.

Another object is to provide an applicator having an end portion formed to catch and hold a suitable adhesive to effect a more dense distribution of the flocking material to the end portion of the applicator.

Another object is to provide an applicator having an end portion with enhanced surface area so as to catch and hold the adhesive applied thereto and thereby creating a more favorable environment for effecting a more uniform and dense distribution of the flocking material thereto.

The foregoing objects and other features and advantages are attained by an applicator having an elongated handle with one end formed for receiving a tuft of bristles to define a brush applicating end and having its other end shaped to maximize the surface area thereof for effecting a more dense and uniform distribution of the flocking material thereto. Also, the applicator of this invention may be provided with a handle formed with a tufted brush at each end thereof, or with a flocked applicating end at each end thereof. With such double ended applicator, there is also provided intermediate the opposed ends of the handle a frangible portion defined as a V-shaped groove circumscribing the handle so as to facilitate the severing of the handle at the defined frangible portion to render the integrally formed double ended applicator into two separate and distinct single ended applicator. One or both ends of the applicator may be provided with an applicator formed of a tuft of bristles to define a brush end or may be coated with a flocking material to define a flocked end. The opposed end portions of the handle adjacent the respective applicating ends are formed so that the applicating end portions or end applicators may be readily bent at an angle relative to the longitudinal axis of the handle.

In accordance with this invention, the applicating end portion of the handle receiving the flocking material is formed so that the surface area thereof is enhanced either by forming the applicating end portion with one or more grooves to increase the surface area thereat, or the applicating end portion may be provided with a series of dimples or depressions to increase the surface area thereof. This arrangement functions to catch and hold the applied adhesive to form a mechanical bond and to which the flocking material can be more uniformly adhered to provide for a more densely flocked applicating end portion capable of retaining a greater amount of material to be applied to a tooth or other surface.

IN THE DRAWINGS

FIG. 1 is a side view of an applicator embodying the present invention.

FIG. 2 is an enlarged view of the applicating end of the applicator of FIG. 1, without the flocking material adhered thereto.

FIG. 3 is a sectional view taken along line 3-3 on FIG. 1.

FIG. 4 is a sectional view taken along line 4-4 on FIG. 1.

FIG. 5 is an enlarged detail view of the frangible portion of the applicator of FIG. 1.

FIG. 6 is an enlarged detailed end view of a modified applicator end portion without the flocking material adhered thereto.

FIG. 7 is a detail side view of a modified applicator end of the present invention with the flocking material removed.

FIG. 8 is a modified embodiment of a double ended applicator.

FIG. 9 is another modified embodiment of a double ended applicator.

FIG. 10 is a fragmentary side view of still another embodiment of the invention.

FIG. 11 is a side view illustrating one type of use of the applicator of FIG. 10.

FIG. 12 is a fragmentary view of another modified embodiment.

FIG. 13 is an partial elevational view of another embodiment.

DETAILED DESCRIPTION

This invention relates to a double ended applicator which is particularly adapted for use in the dental profession, although not limited thereto, of the type initially disclosed in a co-pending application Ser. No. 08/934,983 filed Sep. 22, 1997, for Disposable Dental Applicator. This application, being a continuation-in-part of said co-pending application Ser. No. 08/934,983, now U.S. Pat. No. 6,049,934, incorporates said co-pending application Ser. No. 08/934,983 herein by reference.

Referring to the drawings, there is shown in FIG. 1 one embodiment of the invention. As shown, the applicator 10 includes an elongated handle 11 having opposed applicating end portions 16 and 18 and a frangible means in the form of a circumscribing groove 28 disposed intermediate the opposed ends 16 and 18. The arrangement is such that the elongated handle 11 includes handle sections 12 and 14 which are connected by the frangible means or groove 28.

In the form of the invention illustrated in FIG. 1, the opposed applicating end portions or end applicators 16 and 18 are similarly constructed. As shown, the opposed free ends 20 of the elongated handle 11 are each provided with a pair of spaced apart reduced portions 22, 24 with an enlarged flange or knob 26 disposed therebetween. The arrangement is such that the free ends 20 may be angularly bent relative to the longitudinal axis of the handle 11 at the reduced portion 22 or 24 to dispose the free end 20 at a desired operating angle relative to the axis of the handle, as noted by the phantom showing in FIG. 1. Preferably, the handle 11 is formed of a suitable plastic material capable of maintaining the free ends 20 in a desired bent position, when bent. A suitable plastic for fabricating the handle 11 may be comprised of preferably polypropylene, but can also be made of polystyrene, polyethylene, nylon, and the like. The selected plastic material should be selected so as to be compatible with any anticipated material being applied by the applicator. Thus, the reduced portions 22, 24 function as a hinge about which the free ends 20 may be angularly disposed.

In the embodiment of FIG. 1, the opposed applicating end portion terminates at a tip end 25, which may be generally spherical or elliptical in shape. Adhesively secured to the tip ends 25 are a plurality of flocking fibers 27 which project radially outwardly of the tip end to define the means for containing the dental material to be applied to a tooth. Flocking fibers are minute fibers generally formed of a suitable plastic, e.g. nylon fibers, which are adhered to the respective tip ends 25 by a suitable adhesive.

FIG. 2 is an enlarged showing of the tip end 25 without the attached flocking fibers. As shown, the tip end 25 is generally ellipsoidal in shape having an upper elliptical dome 25A and a lower base 25B which is integrally formed to the adjacent free end 20 of applicator 10. Intermediate the base 25B and the dome 25A, there is provided a circumscribing groove 25C. To secure the flocking fibers to the tip end 25, the tip end is first coated with a layer of adhesive. The groove 25C aids in mechanically bonding the layer of adhesive to the tip end. With the tip end 25 coated with the suitable adhesive, the minute flocking fibers are applied by electrostatically charging the flocking fibers with a polarity opposite to that applied to the tip end 25. Thus, the minute fibers are attracted to and adhered to the tip end 25.

Disposed intermediate the opposed ends 20, the handle is provided with a frangible means which is illustrated as a V-shaped groove 28 circumscribing the outer periphery of the surface of handle 11. Preferably, the sides of the V-shaped grooves define therebetween an angle which approximates a 90° angle. It is to be noted that V-groove 28 enables one to effectively sever the handle 11, when desired, to separate handle section 12 from handle section 14. Thus, the user has the option of using the applicator 10 as a single applicator having opposed applicating end portions or, in the alternative, as two separate and distinct applicators, each having a single applicating end portion.

In order to distinguish one applicator section, e.g. section 12 from applicator section 14, the respective sections 12, 14 may be formed with a different cross-section shape which one may distinguish by touch. For example, handle section 12 may be formed with a round or circular cross-section as noted in FIG. 3. Handle section 14 may be formed with a series of longitudinally extending flutes 34, as best seen in FIG. 4. Thus, if one is applying two different types of materials during a given dental procedure, the dentist can use one applicator section for applying one material, and the other applicator section for applying a different material. Thus, by feel, the dentist can know which applicator section is being used for a given material.

The V-shaped groove 28 defining the angle therebetween enables one to break the handle 11 at the frangible point with a clean break with a minimum of ease, when so desired. As the dentist is normally wearing latex gloves, it is imperative that any severance of handle 11 be made with a clean break which leaves no sharp edges or splinters that may puncture the dentist's protective gloves. The V-shaped groove 28 circumscribing the handle defining the included angle therebetween enables such a clean break.

As the minute flocking fibers are applied to the tip end of the handle 11 by means of an electrostatical charge, the flocking fibers are attracted to the oppositely charged handle so that the fibers are normally disposed, i.e. that they radiate outwardly at right angle to the surface of the tip end 25.

While the embodiment of FIG. 1 illustrates a double ended applicator 10 having opposed ends flocked with minute flocking fibers, a double ended applicator may be provided with a brush formed by a tuft of elongated bristles to define a brush end. Reference is made to FIG. 9 illustrating a double ended applicator 10A, which comprises an elongated handle 30 having disposed intermediate the ends thereof a frangible portion defined by a V-shaped groove 31 similar to that hereinbefore described. Thus, the elongated handle 30 comprises a first section 30A and a second section 30B.

In the form of the invention shown in FIG. 9, the opposed ends of the handle 30 is provided with a bore 32 in which a tuft of bristles 33 is suitably secured to define a brush end. The respective opposed ends are similarly formed. Adjacent the respective opposed ends, the handle is provided with a reduce or crimped portion 34 to function as a living hinge about which the brush end may be bent at an angle relative to the central axis of handle 30. In all other respects, the handle 30 is similar to the handle 11 of FIG. 1.

In use, it will be understood that a dentist is thus provided with the option of utilizing applicator 10A as a single applicator having opposed brush ends which may be used for applying two different materials during a given dental procedure. Or, in the alternative, the dentist may readily separate the respective handle sections 30A and 30B at the frangible portion 31 if only one material is required to be applied in a given procedure, or to use the individual sections 30A, 30B to apply two different materials in a different time sequence. Thus, the double end applicators described herein provides the dentist with a number of options and conveniences not possible with the known brush type applicators and at a more economical cost.

FIG. 8 illustrates another modified embodiment. The applicator 10B of FIG. 8 comprises an elongated handle 40 having a frangible portion 41, similar to that hereinbefore described, to define a first handle section 40A and a handle section 40B. However, in this form of the invention, one end is provided with a brush end 42 and the other end with a flocked end 43. The brush end 42 is formed identically as described in the embodiment of FIG. 9 and the flocked end 43 is similar to the flocked end described in the embodiment of FIG. 1. Handle section 40A is provided with a reduced portion 44 to function as a hinge about which the brush end 42 may be bent relative to the axis of the handle. Likewise, handle section 40B is provided with reduced portions 45, 46 similar to that previously described, about which the flocked end 43 may be bent. In this form of the invention, the user has the convenience of using either the brush end 42 or the flocked end 43 for applying a given material in a given manner, as may be required. In all other respects, the construction and function of applicator 10B is similar to that hereinbefore described.

FIG. 10 illustrates a fragmentary portion of a modified double ended applicator 10C. It will be understood that applicator 10C is a double ended applicator having a frangible portion 41A similar to that described with respect to FIG. 1. Applicator 10C includes a handle section 50B which terminates at its free end in an elongated stem 51 which is sized so as to be inserted into a root canal or post-hole 52 of a tooth 53 to be restored, as best seen in FIG. 11. It will be noted that the stem 51 is connected to the handle section 50B by a reduced web 54 which functions as a hinge about which the stem 51 may be angularly bent relative to the handle section 50B, as seen in FIG. 11.

In this form of the invention, the stem 51 is coated throughout a major portion of its length with minute flocking fibers 55. The flocking fibers are adhesively secured to the stem 51 and extend radially outwardly of the stem about the entire circumference thereof.

With the construction 10C described, the elongated flocked stem 51 is particularly suitable to cleaning out the post-holes and/or root canals. Also, the flocked stem 51 is useful in the placing of dental fluids such as etch, bonding material, cements and the like into hard to reach areas like post-holes or root canals. The construction of FIG. 10C can also function to place medication into a tooth being treated during a root canal therapy or for the placement of medicaments into periodontal pockets.

For the patient, the applicator 10C may be useful for cleaning under dental bridgework, dental implants, periodontal pockets, for delivery of medication such as Peridex or Listerine into periodontal pockets, and may also be used as an interproximal simulator.

It will be understood that the other end (not shown) of the double ended applicator 10C may be constructed similar to the end construction described with respect to FIG. 10 or in the alternative, may be formed with a brush applicator end as hereinbefore described, or with any of the flocked applicator ends herein described. In all other respects, the applicator 10C is similar in operation and construction to the other described embodiment.

It will therefore be apparent that the application 10C can be professionally used by the dentist and also by the patient for continued home care to insure and maintain better oral health.

FIG. 6 is directed to an enlarged detail view of modified applicating end 116, without the flocking fibers attached, which may be embodied in the double ended applicators described herein. As shown, the free end 120 of a double ended applicator 10D is provided with a spheriodal surface 130 having a series of concentric slots 132 formed therein. The slots 132 function to provide a mechanical bond of the adhesive (not shown) which is applied to the tip end and also serves to increase the surface area of the applicating end 116, to which the flocking fibers adhere to provide for a more dense population of adhered flocking fibers, for retaining a greater supply of material to be applied to a tooth. The tip end 120 is hingedly connected to the handle section 112 by means of a reduced area or web 122, 124 in a manner hereinbefore described.

The primary requirement of a flocked applicator as described herein is that it be small and still be capable of holding an adequate amount of material to perform the desired procedure. As will be described herein, the flocked applicators embody a construction to provide for an increased surface area for receiving the flocking fibers. As the flocked applicators described with respect to FIG. 6 is quite small, the portions defining the slots are flexible and will tend to flex, rendering it more gentle when pressed or rubbed against any soft or tender tissue as may be encountered in a given dental procedure.

Referring to FIG. 7, the free end 140 of an applicator 10E, illustrated without the flocking fibers adhered thereto, is formed generally ellipsoidal, having formed on the surface thereof a series of depressions or cavities 141 which are capable of forming a mechanical bond with the adhesive coating (not shown) applied thereto. The arrangement is such that when the flocking fibers are applied to the adhesively coated end 140 by the electrostatic method herein described, the fibers will radially adhere to the exposed surfaces which are both concave in part and convex in part, the cavities 141 defining the concave surfaces. As the arrangement provides for a greater exposed surface area, more flocking fibers will be adhered to the exposed surfaces to define a more dense population of flocking fibers extending outwardly in a radial direction over the entire exposed surface. The tip end 140 is hingedly connected to handle section 142 of applicator 10E by reduced portions or webs 143, 144 similar to that hereinbefore described. In all other respects, the structure and function is similar to that hereinbefore described.

FIG. 12 illustrates another modified embodiment of an applicator end portion for use in a double ended applicator 10F. The end applicator portion 150 of FIG. 12 comprises a stem 151 having integrally formed thereon a helical plane 152 which coils about the stem 151. It will be understood that the individual coils of the helical plane 152 have a diameter that may be either equal or different from one another, with a pitch which may be the same or varied over the length thereof. In this form of the invention, the helical plane 152 is coated with a suitable adhesive, to which the flocking fibers are adhered or applied by the electrostatic process herein described. It will be noted that the helical plane 152 provides for an enhanced surface area to which the flocking fibers adhere in a pattern and arrangement to absorb and hold larger amounts of a dental material to be applied.

As shown in FIG. 12, the applicating end portion 150 is hingedly connected to the handle section 153 by reduced webs 154, 152 similar to that hereinbefore described.

In all other respects, the applicator 10E is similar to that hereinbefore described.

FIG. 13 illustrates another embodiment of the present invention. In this embodiment applicator 216 has a hemispherical portion 230 and a conical portion 231. Line 232 separates the hemispherical portion 230 and the conical portion 231. Neck 220 connects the conical portion 231 to the handle 242. In other respects the applicator is similar to the other embodiments illustrated. The hemispherical portion 230 provides good adhesive retention and resulting flocking at the distal end, while the conical section 231 provides adhesive to the hemispherical portion from an area that may not need the same degree of flocking as the distal end.

From the foregoing description, it will be noted that the double ended applicators provide the dentist with a number of options not previously available in applying various dental materials to a tooth by the use of a single applicator in applying two different materials, as is commonly the case. Also, the applicator may be provided with commonly constructed applicating end portions or may have differently constructed applicating end portions, depending upon a given procedure.

While the described embodiments of this invention have particular application in the field of dentistry, the applicators may also have utility in certain industrial applications where precision is required and/or in certain crafts and hobby related work.

While the present invention has been described with respect to particular embodiments, modifications and variations may be made without departing from the spirit or scope of this invention.

What is claimed is:

1. A disposable dental material applicator comprising:
   a handle;
   an elongated stem having a longitudinal length attached to said handle;
   flocking fibers coated on a major portion of the longitudinal length of said elongated stem;
   a second elongated stem having a second longitudinal length attached to a second end of said handle;
   second flocking fibers coated on a second major portion of the second longitudinal length of said second elongated stem; and
   a V-shaped groove circumscribing said handle to define a first handle section and a second handle section,
   whereby the first handle section is capable of being separated from the second handle section.

2. An integrally formed disposable dental applicator comprising:
   an elongated handle,
   an elongated stem integrally connected to said handle at one end thereof to define a unitary member, and including
   a reduced web connected between said elongated handle and said elongated stem to define an integrally formed hinge permitting said elongated stem to be optionally bent at an angle relative to said elongated handle,
   said elongated stem being sized and shaped for adapting said elongated stem to be received within a root canal or post hole formed in a tooth,
   and minute flocking fibers adhesively secured to said elongated stem that extend radially outwardly about said elongated stem,
   said flocking fibers extending from the free end of said elongated stem and along the length of said elongated stem a distance substantially equal to the depth of a root canal or post hole of a tooth.

3. An integrally formed disposable dental applicator as defined in claim 2 wherein said elongated stem includes a smooth outer surface throughout the length thereof.

4. An integrally formed disposable dental applicator as defined in claim 3 wherein said minute flocking fibers are randomly adhered about the entire circumference of said elongated stem throughout the flocked length thereof.

5. An integrally formed dental applicator as defined in claim 4 wherein said elongated handle, elongated stem and connected reduced web are integrally formed of a moldable plastic material.

\* \* \* \* \*